United States Patent [19]
Dahl et al.

[11] Patent Number: 5,366,496
[45] Date of Patent: Nov. 22, 1994

[54] SUBCUTANEOUS SHUNTED COIL ELECTRODE

[75] Inventors: Roger W. Dahl, Andover; Jayne G. Fangel, White Bear Lake, both of Minn.; David K. Swanson, Mountain View, Calif.

[73] Assignee: Cardiac Pacemakers, Inc., St. Paul, Minn.

[21] Appl. No.: 41,096

[22] Filed: Apr. 1, 1993

[51] Int. Cl.⁵ ............................................. A61N 1/36
[52] U.S. Cl. .................................... 607/132; 607/119
[58] Field of Search ............... 607/116, 129, 132, 122, 607/123

[56] References Cited

U.S. PATENT DOCUMENTS

| | | |
|---|---|---|
| 3,333,045 | 7/1967 | Fisher et al. |
| 3,474,791 | 10/1969 | Bentov .............................. 607/132 |
| 3,543,761 | 12/1970 | Bradley |
| 3,760,812 | 9/1973 | Timm et al. |
| 3,866,615 | 2/1975 | Hewson |
| 4,006,748 | 2/1977 | Schulman |
| 4,030,509 | 6/1977 | Heilman et al. |
| 4,270,549 | 6/1981 | Heilman |
| 4,291,707 | 9/1981 | Heilman et al. |
| 4,314,095 | 2/1982 | Moore et al. |
| 4,522,212 | 6/1985 | Gelinas et al. |
| 4,530,368 | 7/1985 | Saulson et al. ...................... 607/132 |
| 4,567,900 | 2/1986 | Moore |
| 4,603,705 | 8/1986 | Speicher et al. |
| 4,641,656 | 2/1987 | Smits |
| 4,760,852 | 8/1988 | Lekholm |
| 4,774,952 | 10/1988 | Smits |
| 4,817,634 | 4/1989 | Holleman et al. |
| 4,938,231 | 7/1990 | Milijasevic et al. |
| 5,005,587 | 4/1991 | Scott |
| 5,016,645 | 5/1991 | Williams et al. |
| 5,042,463 | 8/1991 | Lekholm |
| 5,044,374 | 9/1991 | Lindemans et al. |
| 5,044,375 | 9/1991 | Bach, Jr. et al. |
| 5,203,348 | 4/1993 | Dahl |

FOREIGN PATENT DOCUMENTS

| | | |
|---|---|---|
| 0529945 | 7/1954 | Belgium |
| 0211166 | 2/1987 | European Pat. Off. |
| 347353A | 6/1989 | European Pat. Off. |
| 0706582 | 6/1931 | France |

OTHER PUBLICATIONS

Cardiac Pacing and Electrophysiology Proceedings of VIII World Symp. on C.P. and Elephys., Jerusalem, Israel, Jun. 7-11, 1987, Belhassen Feldman and Copperman (Eds) "Electrode System for Closed Chest Ventricular Defibrillation" (Obel et al) pp. 465-472.

"Nonthoracotomy Internal Defibrillation in Dogs: Threshold Reduction Using a Subcutaneous Chest Wall Electrode With a Transvenous Catheter Electrode" Jule Wetherbee *JACC*, vol. 10, No. 2, Aug. 1987:406-11.

Primary Examiner—William E. Kamm
Assistant Examiner—Scott M. Getzow
Attorney, Agent, or Firm—Haugen and Nikolai

[57] ABSTRACT

A body implantable cardioversion/defibrillation device includes an electrically conductive lead, three lead extensions coupled to the lead through a junction body, and an electrode array consisting of three electrodes, one electrode being coupled to each of the lead extensions. Each electrode has several separate electrically conductive paths, including a primary conductor in the form of a helically wound coil, and a linear shunt conductor in the form of a cable surrounded by the primary coil. The shunt cable is a composite, including a DBS core surrounded by an insulative coating. A dielectric sheath surrounds the shunt cable, preventing the cable from contacting the primary coil and isolating the shunt cable from contact with body tissue or body fluids. At each end of each electrode is a connector structure including a shunt connector attached to an end of the shunt cable, and an outer coil connector surrounding an end of the primary coil and the shunt connector. Both connectors are crimped to maintain the electrical and mechanical coupling. The junction body includes an electrically conductive plate having several bores directed inwardly into the plate. A thin wall portion on one side of each bore can be crimped following insertion of each lead or lead extension, to secure the electrical and mechanical connection.

26 Claims, 5 Drawing Sheets

SUBCUTANEOUS SHUNTED COIL ELECTRODE

BACKGROUND OF THE INVENTION

The present invention relates to electrical defibrillation, including cardioversion, and more particularly to body tissue stimulation electrodes, implanted subcutaneously in the thoracic region, for delivering cardioversion/defibrillation pulses.

Defibrillation is a technique employed to counter arrhythmic heart conditions including tachycardias, flutter and fibrillation of the atria and/or the ventricles. Typically, electrodes are employed to stimulate the heart with electrical impulses or shocks, of a magnitude substantially greater than pulses used in cardiac pacing. One approach to defibrillation involves placing electrically conductive paddle electrodes against the chest of the patient. During cardiac surgery, such paddles can be placed directly against the heart to apply the necessary electrical energy.

More recent defibrillation systems include body implantable electrodes. For example, patch electrodes can be applied directly to epicardial tissue. Electrodes can be placed at the distal end region of an intravascular catheter inserted into a selected cardiac chamber. U.S. Pat. No. 4,60,705 (Speicher et al) discloses an intravascular catheter with multiple electrodes, employed either alone or in combination with an epicardial patch electrode. Compliant epicardial defibrillator electrodes are disclosed in U.S. Pat. No. 4,567,900 (Moore), and in U.S. Pat. No. 5,105,826 (Smits et al).

Epicardial electrodes are considered efficient in the sense that less pulse generator energy is required for delivering effective defibrillation pulses. However, epicardial electrode implantation typically requires highly invasive major surgery including entry of the chest cavity, typically involving the spreading of adjacent ribs or splitting of the sternum, presenting a risk of infection. Epicardial electrodes must either be quite small, or highly compliant and resistant to fatigue, as they must maintain a conformal fit to the epicardium.

Larger defibrillation electrodes usually are preferred, since increasing the electrode size reduces impedance at or near the electrode. Sensing artifacts also are reduced. However, the larger electrodes are more difficult to attach to the epicardium and are more subject to fatigue, as they must conform to the heart during contractions associated with normal cardiac activity.

Subcutaneous defibrillation electrodes are easier to implant, and the implant procedure involves less risk to the patient. To achieve a large effective electrode area and yet maintain patient comfort to the extent possible, defibrillation can be accomplished with an array of several electrodes or electrode segments spaced apart from one another, as disclosed in U.S. Pat. application Ser. No. 07/533,886 filed Jun. 6, 1990, assigned to the assignee of this application. The electrode segments are relatively long and narrow, and are coupled to a single electrically conductive lead for simultaneous delivery of the defibrillation pulse. The electrode segments are highly compliant, and can be formed of composite conductors in the form of titanium or tantalum ribbons or wires, or a cable consisting of a silver core in a stainless steel tube. In either case, an outer layer of platinum can be applied by sputtering, or cladding after applying a Tantalum layer for adhesion. A braided construction also can impart compliance to an elongate electrode or electrode segment, as disclosed in U.S. Pat. No. 5,005,587 (Scott).

In view of the greater efficacy of large effective shocking area electrodes, longer electrodes and electrode segments are preferred. However, as an electrode of a given diameter becomes longer, its impedance increases, as does the voltage drop from the electrode proximal end to the electrode distal end. This leads to an unwanted gradient in interelectrode current distribution. Typically the conductive path is substantially longer than the linear length dimension of the electrode, because of the common practice of configuring electrodes as helically wound coils to enhance their fatigue resistance and ability to continually conform to body tissue. Of course, the diameter of the strand forming the coil electrode can be increased to improve its conductivity. However, this also increases electrode stiffness and patient discomfort. A further constraint arises from the fact that the electrode is in surface contact with body tissue. Accordingly, electrode materials must be body compatible as well as electrically conductive. Certain materials with highly favorable conductivity and fatigue properties are unavailable for use in such electrodes.

Therefore, it is an object of the present invention to provide an elongate electrode that is highly conductive in spite of a relatively small diameter and lateral cross section.

Another object is to provide a body implantable tissue stimulating electrode of considerable length, yet substantially uniform in potential (voltage) level from its proximal end to its distal end.

A further object is to provide an electrode structure incorporating a primary conductive path in contact with body tissue, and a conductive shunt path with a fluid tight sealing means preventing the shunt path from contacting body fluids or body tissue.

Yet another object is to provide a cardioversion/defibrillation electrode array having a high degree of redundancy.

SUMMARY OF THE INVENTION

To achieve these and other objects, there is provided a body implantable tissue stimulating device. The device includes an elongate, flexible electrically conductive lead, and a tissue stimulating electrode array having at least two electrodes, electrically common in the sense of being coupled to the lead for receiving pulses simultaneously. Each electrode includes a body compatible primary conductor providing a convoluted electrically conductive path from a first end region of the electrode to a second and opposite end region of the electrode. The primary conductor has an exposed surface over substantially all of its length, to promote transfer of electrical impulses to adjacent body tissue. Each electrode also has a shunt conductor adjacent to the primary conductor and providing a substantially linear electrically conductive shunt path between the first and second end regions. The primary conductor and the shunt conductor are electrically coupled at the first and second end regions. A fluid impermeable means surrounds the shunt conductor to prevent the shunt conductor from contacting body tissue or body fluids. The first end region of each electrode is coupled with respect to a distal end region of the lead, to enable the electrode to receive tissue stimulating electrical pulses from a pulse generating means at a proximal end of the lead.

Preferably the tissue stimulating electrode array includes three of the electrodes. With the first end of each electrode electrically coupled to the lead, pulses from the pulse generator are provided simultaneously to all three electrodes. As a result, the electrodes, when spaced apart from one another, provide an effective shock area having a boundary surrounding all of the electrodes. The advantages of this configuration are explained in the aforementioned 533,886 application.

The electrode array provides substantial redundancy for reliable long term performance. For example, should a break or other interruption occur in one of the primary conductors, the shunt conductor remains available to transmit the electrical pulses, albeit with an increase in the voltage gradient across the electrode. The three-electrode array provides further redundancy in that a complete failure of one of the electrodes still leave two fully operative electrodes, with but a slight reduction in shock efficacy.

The preferred configuration for the primary conductor is a helically wound coil, for resistance to fatigue and conformity to body tissue. The primary conductors can be formed of low resistance composite conductors including drawn braised strands (DBS), and drawn filled tubes (DFT) coated with platinum or another metal from the platinum group. A multifilar (multiple filament) construction can be used in the primary conductor, for further redundancy.

The preferred shunt conductor comprises a conductive cable, wire, or coil, e.g. a DBS cable or multifilar wire. High conductivity and fatigue resistance are the key factors in selecting the shunt conductor materials.

In one preferred approach, a dielectric coating is applied to the exterior surface of the shunt conductor, and a flexible, dielectric tubing surrounds the shunt conductor. The tubing, in turn, is surrounded by the helically wound coil. At each end of the electrode, a crimp connecting arrangement is employed to electrically couple the primary and shunt conductors, and at the same time mechanically couple the conductors. A medical adhesive is applied at the contact areas, to insure a fluid tight seal between the dielectric sleeve and the shunt conductor. Thus, the shunt conductor is completely isolated from contact with body tissue or body fluids, substantially eliminating any injury to the body or corrosion of the shunt conductor that might arise from such contact. As a result, materials that are highly conductive and fatigue resistant, yet not as well suited for direct contact with bodily tissue and fluids, can be considered for construction of the shunt path.

The primary conductor and shunt conductor provide parallel electrically conductive paths for increased electrode conductivity. This reduces the voltage gradient (difference in voltage levels at the electrode proximal end and distal ends) to ensure effective delivery of cardioversion pulses, even for electrodes in the range of ten to thirty centimeters in length, and with primary coil and shunt cable diameters of 0.080 inches and 0.025 inches, respectively. The absence of any substantial voltage gradient end to end over the electrode length, and appropriate spacing (at least 1.5 centimeters) between adjacent electrodes of the array, substantially improve the uniformity in the interelectrode current distribution over the effective electrode shock area.

Another aspect of the present invention is a body implantable tissue stimulating system including a stimulation pulse generator, a tissue stimulating electrode array implanted at least proximately thoracic region, a first coupling means electrically coupling the tissue stimulating electrode array and the pulse generator, a tissue stimulating electrode configuration implanted at least proximate the thoracic region and spaced apart from the electrode array, and a second coupling means, electrically isolated from the first coupling means, for coupling the pulse generator and the electrode configuration.

The electrode configuration can consist of one or several tissue stimulating electrodes. For example, a unitary cardioversion catheter, inserted into the right ventricle, can provide an electrode configuration consisting of one or more cardioversion electrodes in the form of coils or springs. More particularly, the catheter can position a cardioversion coil within the right ventricle and another coil near the superior vena cava. Yet another cardioversion coil electrode can be positioned in the region of the subclavian vein or of the third to seventh intercostal space. Alternatively, the electrode configuration can take the form of a myocardial patch electrode.

The tissue stimulating electrode array has at least two electrically common electrodes. Each electrode includes a primary conductor providing an electrically conductive path from a first end portion of the electrode to a second and opposite end portion of the electrode. The primary conductor is exposed over most of its length for contact with body tissue and body fluids. The first electrode also includes a shunt conductor providing a substantially linear shunt path between the first and second end regions. The primary and shunt conductors are electrically coupled to one another at the first and second end regions. A means is provided for isolating the shunt conductor from any contact with body tissue or body fluids.

A preferred system includes three such electrodes in the tissue stimulating electrode array, substantially identical in construction to one another and coupled to the pulse generator via the first coupling means. As a result, the three electrodes simultaneously receive pulses from the pulse generator.

The first coupling means preferably includes an electrically conductive lead with its proximal end coupled to the pulse generator, and a junction body connected to the distal end of the lead and to the first, third and fourth electrodes. The junction body has an electrically conductive core and a biocompatible, dielectric shell surrounding the conductive core. The coupling means also can include three electrically conductive lead extensions, with each lead extension coupled between the junction body and a corresponding one of the three electrodes of the array. Four bores are formed into the thickness of the junction body core. Three of the bores receive respective proximal ends of the lead extensions, whereupon the core is conveniently crimped to provide secure joints retaining the lead extensions, and further to provide the electrical connections. This feature, in combination with the above-mentioned connecting arrangement, significantly reduces the cost of manufacturing the tissue stimulation device.

Thus, according to the present invention, a cardioversion/defibrillation device employs elongate subcutaneous electrodes, spaced apart from one another to provide an electrode array of highly electrically conductive, compliant and fatigue resistant electrodes. Redundancy is provided by the number of electrodes, the shunt conductor as an alternative signal path, and, if desired, a multifilar construction of the primary conductor and shunt conductor. This electrode construction enables use of electrodes having considerable length and small diameters, yet with increased uniformity in interelectrode current distribution. The subcutaneous electrode array is surgically implanted with reduced trauma and hematoma, and with substantially improved comfort to the patient following implant.

IN THE DRAWINGS

For a further understanding of the above and other features and advantages, reference is made to the following detailed description and to the drawings, in which.

DETAILED DESCRIPTION OF THE PREFERRED EMBODIMENT

Figure 1:
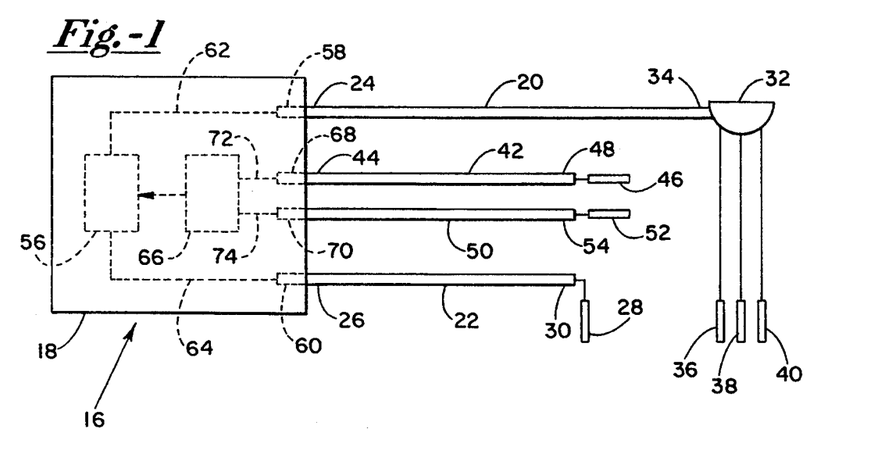
FIG. 1 is a schematic view of a cardioversion/defibrillation system employing a tissue stimulation device constructed according to the present invention.

Turning now to the drawings, there is shown in FIG. 1 a cardioversion/defibrillation system 16 for selectively applying relatively high energy electrical shocks to the heart, a technique frequently referred to as cardioversion. Typically the system includes a means for sensing an abnormally rapid cardiac rhythm. In response to sensing such rhythm, a high energy shock is discharged through electrodes contiguous with cardiac tissue, to depolarize and restore the heart to normal cardiac rhythm.

System 16 includes a cardioversion control unit 18, and two elongate electrically conductive leads 20 and 22 coupled to the cardioversion control unit at their respective proximal ends 24 and 26. A single electrode 28 in the form of a helically wound coil is connected at a distal end 30 of lead 22. A lead/electrode junction body 32 is electrically and structurally connected to a distal end 34 of lead 20. An electrode array consists of three helical coil electrodes 36, 38 and 40 coupled to the junction body.

A cardiac sensing portion of the system includes an electrically conductive sensing lead 42 coupled at its proximal end 44 to the cardioversion control unit, a sensing electrode 46 at the distal end 48 of lead 42, a second sensing lead 50 coupled at its proximal end to the control unit, and a sensing electrode 52 at the distal end 54 of lead 50.

Cardioversion control unit 18 includes a cardioversion pulse generating circuit, represented schematically at 56. The control unit has two receptacles 58 and 60 for receiving leads 20 and 22, respectively. The receptacles are coupled to the pulse generating circuit, as indicated in broken lines at 62 and 64. The control unit further includes a pulse or heart rate sensing circuit represented in broken lines at 66. A pair of receptacles 68 and 70 receive the respective proximal ends of sensing leads 42 and 50, for electrical coupling to the sensing circuit, as indicated in broken lines at 72 and 74. Sensing circuit 66 and cardioversion circuit 56 are operatively coupled to one another, in that when an abnormal rhythm or pulse rate is detected in sensing circuit 66, cardioversion circuit 56 is triggered to deliver one or more cardioversion pulses.

Lead 20, junction body 32 and the electrode array combine to form a tissue stimulation device particularly well suited for subcutaneous placement in the thoracic region. A cardioversion/defibrillation system may incorporate one of these devices in combination with a single endocardial positioned electrode such as electrode 28. Alternatively, a system may include two such stimulation devices, positioned on opposite sides of the heart for transthoracic delivery of tissue stimulating pulses.

Figure 2:
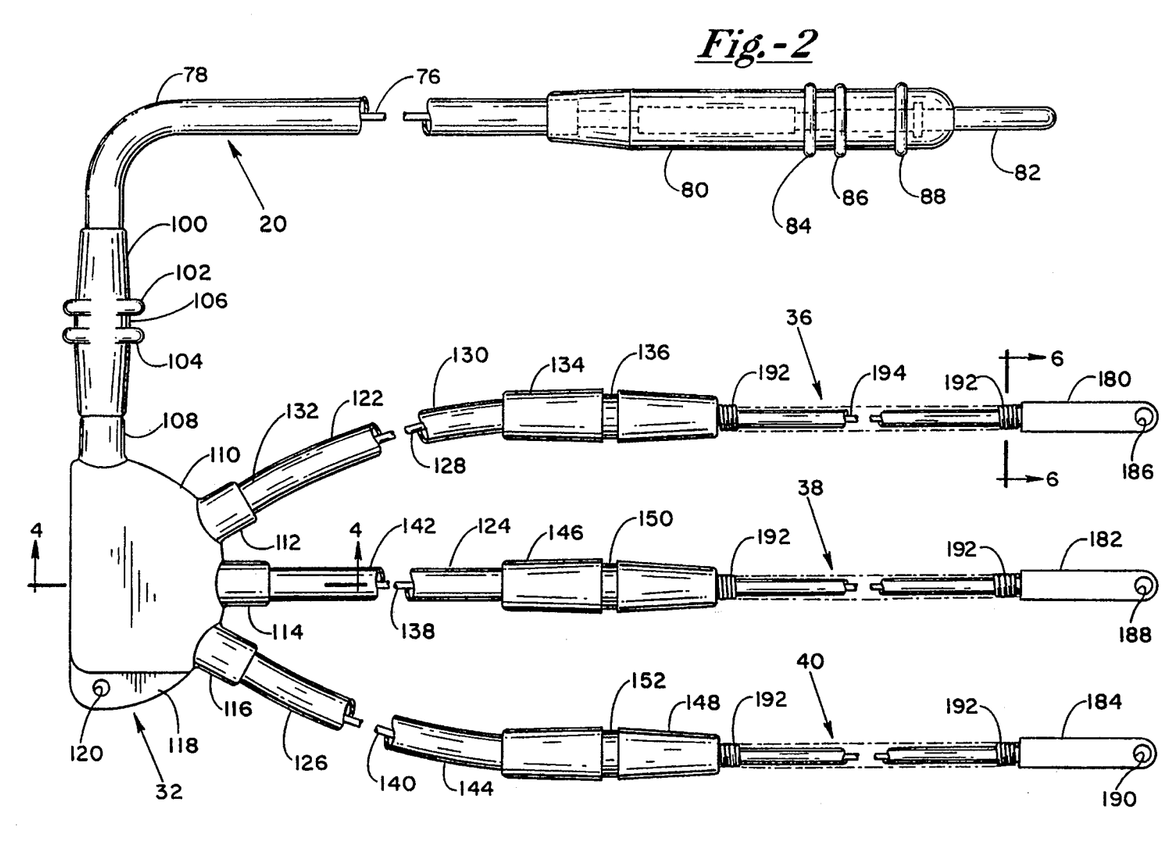
FIG. 2 is a plan view of the tissue stimulation device.

FIG. 2 illustrates the tissue stimulation device in greater detail. Lead 20, over the majority of its length of about 18 inches, consists of an electrically conductive cable 76 contained within a dielectric sheath 78. The cable can be of drawn braised strand (DBS) construction, or it can be a multi filament cable. In either event, cable 76 must exhibit high electrical conductivity in combination with flexibility, pliability and fatigue resistance. Sheath 78 likewise must be flexible, and is constructed of a body compatible polymer, e.g. silicone rubber or polyurethane.

At the proximal end of sheath 78 is an electrically insulative boot 80. The boot is connected to sheath 78 in fluid tight fashion and surrounds the sheath. The boot also surrounds an electrically conductive pin 82 at the proximal end of the lead. Cable 76 and pin 82 are electrically coupled in a known manner, not germane to the present invention and thus not shown or described further. Boot 80 includes three annular ribs 84, 86 and 88. These ribs are slightly elastically deformed when the boot is inserted into receptacle 58 of control unit 18, thus to maintain a fluid tight seal when the boot is contained within the receptacle. At the distal end of the lead, a strain relief sleeve 100 surrounds the sheath. Sleeve 100 is constructed of a suitable body compatible polymer, e.g. silicone rubber. Ribs 102 and 104 surround strain relief sleeve 100, and define a groove 106 that facilitates suturing sleeve 100 to body tissue.

The strain relief sleeve is shown against an electrically insulative strain relief extension 108 of junction body 32. The junction body has a dielectric casing 110, with three further strain relief extensions 112, 114 and 116 forming part of the casing. Also extending from the casing, downwardly as viewed in FIG. 2, is a reduced-thickness region 118. An aperture 120, formed through region 118, facilitates securing junction body 32 to body tissue using sutures.

Three lead extensions 122, 124 and 126 are coupled to the junction body. Lead extension 122 includes an electrically conductive Teflon coated cable 128 surrounded by an electrically insulative sheath 130. Sheath 130, at its proximal end 132, is contained within strain relief extension 112, and forms a fluid tight seal with the strain relief extension. At the distal end, sheath 130 is surrounded by a strain relief sleeve 134, again coupled to provide a fluid tight seal. Strain relief sleeve 134 includes a groove 136 to facilitate suturing the sleeve to body tissue.

Lead extensions 124 and 126 are substantially identical to lead extension 122 in construction, and include respective cables 138 and 140, sheaths 142 and 144, and strain relief sleeves 146 and 148 with suturing grooves 150 and 152. The cables, sheaths and strain relief sleeves of the lead extensions are similar to their counterparts of lead 20, and can be constructed of the same materials. The sheaths are dielectric and resilient, and the cables are electrically conductive, highly compliant and fatigue resistant.

Figure 3:
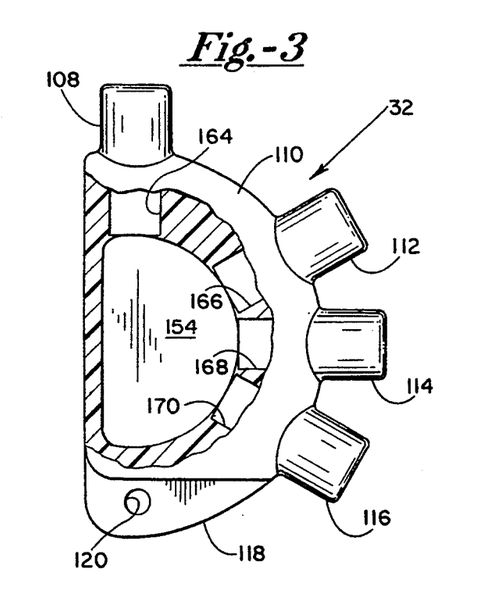
FIG. 3 is an enlarged view of a lead/electrode junction body of the device.

In FIG. 3, portions of dielectric casing 110 have been removed to reveal a core or junction plate 154 contained within the casing. Plate 154 has an exterior profile resembling that of the letter "D", and is planar and flat, with a nominal thickness of about 1/22 of an inch (0.045 inches). Plate 154 is constructed of a body compatible metal, e.g. titanium, and forms the electrical and mechanical coupling between lead 20 and the lead extensions. Four bores 156, 158, 160 and 162 (FIG. 5) are formed in plate 154, parallel to the major plane of the plate. Bore 156 receives the distal end of cable 76. Each of bores 158, 160 and 162 receives the proximal end of its associated lead extension cable, i.e. one of cables 128, 138 and 140. Openings through casing 110 and the strain relief extensions, as indicated at 164, 166, 168 and 170, accommodate the lead cable and lead extension cables and their respective sheaths.

Figure 4:
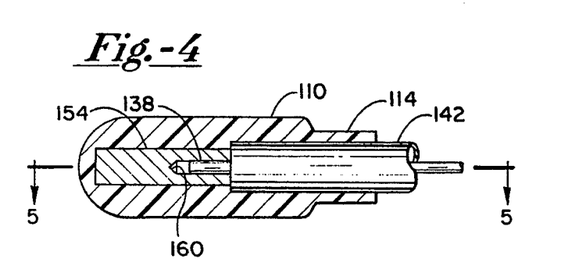
FIG. 4 is a sectional view taken along the line 4—4 in FIG. 2.
Figure 5:
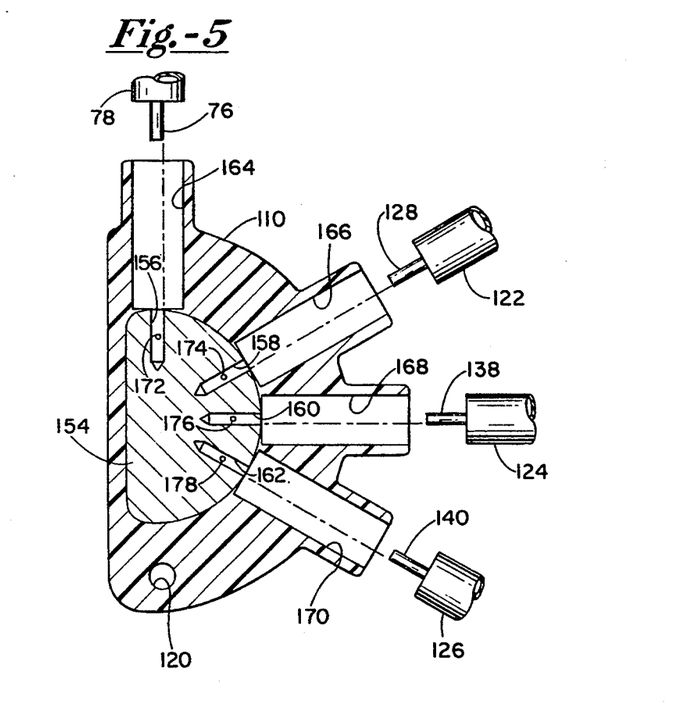
FIG. 5 is a partial sectional view taken along the line 5—5 in FIG. 4.

FIGS. 4 and 5 illustrate plate 154 and the manner in which the cables are coupled to the plate. Bores 156, 158, 160 and 162 have diameters in the range of about 0.021 inches, oriented in the direction of the plate thickness. Each bore is intentionally offset from a centered relation relative to the plate thickness. Thus, a pair of side wall portions are formed on opposite sides of each bore, one of the wall portions being relatively thin and constituting a crimp wall portion. Given the 1/22 of an inch thickness of the plate, each 0.021 inch diameter bore preferably is offset to provide a crimp wall thickness of about 0.009 inches.

Junction plate 154 facilitates a quick and convenient coupling of lead 20 with lead extensions 122, 124 and 126. The connection is completed before dielectric casing 110 is molded on and about plate 154. More particularly, each of the lead cables is inserted by its end into its associated one of bores 156, 158, 160 and 162. With each cable so inserted, junction plate 154 is selectively crimped to secure the cables in place and make the electrical connection. Dots at 172, 174, 176 and 178 identify preferred crimping locations. The crimping operation is similar to the crimping of well known cylindrical crimp tubes. There is a difference, however, in that the crimping of plate 154 involves plastic deformation of the relatively thin crimping side wall portion of each bore, simultaneous with the elastic deformation of the cable end portion contained within the bore. The elastic deformation is slight, but sufficient to create a connection able to withstand tensile forces well beyond any expected during or after implant of the device. After crimping is completed, casing 110 is formed on and about junction plate 154 by a molding process.

The electrode array in FIGS. 1 and 2 includes three tissue stimulating electrodes 36, 38 and 40 electrically and mechanically coupled to lead extensions 122, 124 and 126, respectively. At its distal end, each of the electrodes is connected to an electrically conductive tubular end cap, as shown at 180, 182 and 184. The distal end caps have respective apertures 186, 188 and 190 to facilitate suturing the caps to body tissue, to secure the electrode array.

Figures 6, 7:
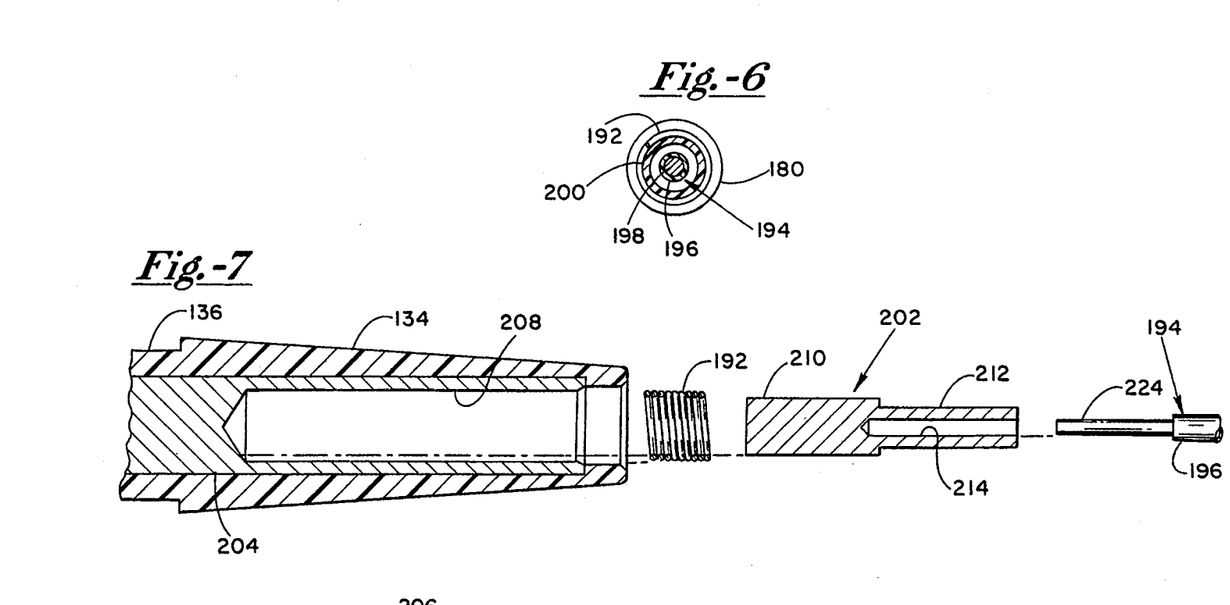
FIG. 6 is a sectional view of one of the electrodes, taken along the line 6—6 in FIG. 2.
FIG. 7 is a fragmented parts view of a proximal coupling structure of the device.

Each electrode incorporates several electrically conductive paths, as perhaps best seen in FIG. 6 with respect to electrode 36. The electrode includes an outer, primary conductor 192 in the form of a helically wound coil, or alternatively several helically wound coils intermingled to present the appearance of a single helical coil. The helical configuration enhances the ability of the electrode to conform to contours within the body, and to continually and repeatedly adjust to the changes in body tissue contours caused by normal muscular activity. Primary coil conductor 192 can be of multifilar (multifilament), DFT or clad construction, utilizing outer layers of body compatible metals such as platinum, other metals in the platinum group, or alloys of these metals.

Primary coil conductor 192 surrounds a secondary conductor or shunt cable 194. Shunt cable 194 can be of multifilament or DBS construction, and must exhibit high electrical conductivity, fatigue strength and compliance to body tissue contours. Preferably, shunt cable 194 is constructed of a DBS composite of stainless steel and silver or other body compatible metals. A dielectric coating 196 of tetrafluoroethylene (TFE, available under the brand name Teflon) is applied to a conductive core 198 along most of the shunt cable length.

A tubular sheath 200, constructed e.g. of silicone rubber, surrounds shunt cable 194 in a close but spaced apart relation to the cable. The sheath and shunt cable thus are free of one another along most of the electrode length. This allows limited axial movement of these components relative to one another, enhancing the compliance of the electrode. It is to be understood that electrodes 38 and 40 are substantially identical in construction to electrode 36.

Figure 8:
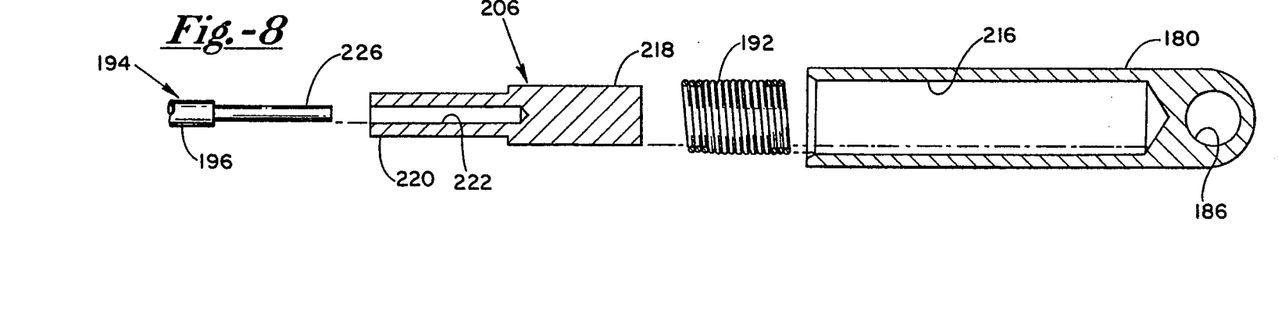
FIG. 8 is a fragmented parts view of a distal coupling structure of the device.

A unique connector structure facilitates assembly of the electrodes, as illustrated in FIGS. 7 and 8 for electrode 36. Components of the structure include a tubular proximal shunt connector 202, a tubular proximal coil connector 204 within strain relief sleeve 134, a tubular distal shunt connector 206, and a distal coil connector, i.e. end cap 180. All of these connectors preferably are constructed of a body compatible metal, e.g. titanium or a cobalt based alloy known as MP35N. Proximal coil connector 204 is part of a larger connector structure (not shown) embedded within strain relief sleeve 134. An elongate central opening 208 extends proximally into connector 204.

Proximal shunt connector 202 includes a head 210, and a shank portion 212 with a reduced outer diameter as compared to the outer diameter of the head. The outer diameter of head 210 is less than the inner diameter of opening 208, by an amount sufficient to accommodate a proximal portion of primary coil 192 between coil connector 204 and head 210, when shunt connector 202 is contained within opening 208. A cable receptacle 214 is open to the distal end of shunt connector 202, and extends proximally beyond shank 212 into head 210.

An opening 216 is formed into end cap 180, and extends along most of the end cap length in the direction toward suture aperture 186. Distal shunt connector 206 includes a head 218, a reduced diameter shank 220 and a cable receptacle 222 along the shank and part of the head. The head diameter is less than the inside diameter of opening 216 to permit insertion of shunt connector 206, surrounded by the distal end portion of primary coil 192, into opening 216.

Electrode 36 is assembled, first by stripping the dielectric Teflon layer away form the proximal and distal ends of shunt cable 194, leaving exposed end portions 224 and 226. End portion 226 is inserted into receptacle 222 of shunt connector 206, until the Teflon coating abuts the proximal end of the shunt connector. Next, the shunt connector is crimped along shank 220 to permanently join the connector and the shunt cable.

A medical grade adhesive is applied to the outside surface of shank 220. Then, tubular sheath 200 is inserted distally over the shunt cable and onto the shunt connector, until the distal end of sheath 200 is contiguous with head 218. The adhesive cures, bonding sheath 200 to shank 220.

With the distal end coupling thus complete, exposed end 224 of shunt cable 194 is inserted into receptacle 214 of proximal shunt connector 202 until the Teflon layer abuts the distal end of connector 202. This insertion is followed by a crimping of the proximal connector along the mid portion of shank 212. Adhesive is applied to the outer service of the shank, whereupon dielectric sheath 200, already surrounding the shunt cable, is pushed onto the shank, to the point of contact with head 210.

Next, primary coil conductor 192 is inserted over the sheath and shunt cable. The distal shunt connector and coil are inserted distally into opening 216 of the distal coil connector (i.e. end cap 180), until the distal ends of the coil and shunt connector contact the distal end of opening 216. At this point, end cap 180 is crimped to secure the primary coil, distal shunt connector, cable and sheath with respect to the end cap.

Finally, proximal connector 202 and the proximal end of primary coil 192 are inserted into opening 208 of coil connector 204. The coil connector is crimped to complete the connection.

Figure 9:
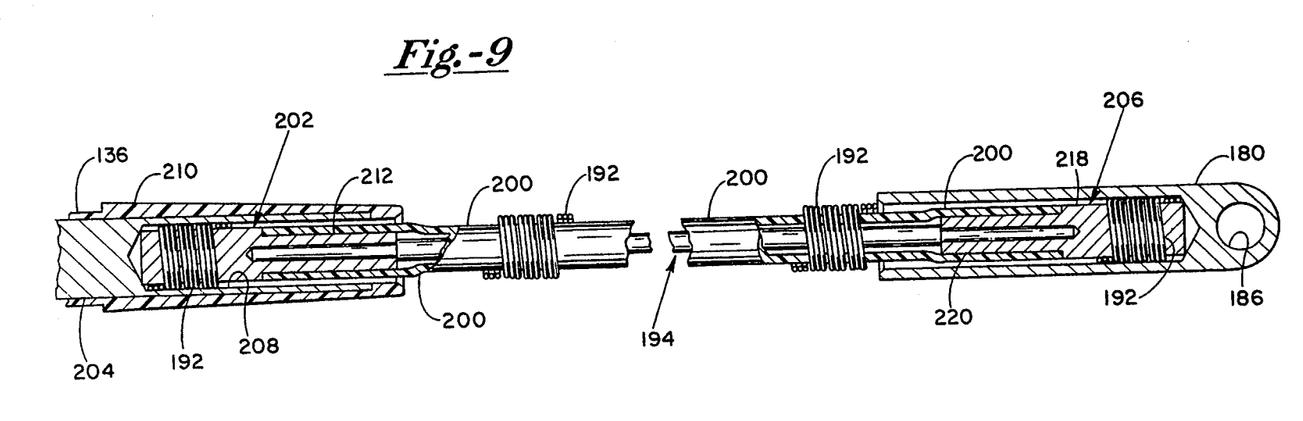
FIG. 9 is a plan view, partially in section, showing one of the device electrodes.

Thus, the proximal end and distal end coupling are complete. At each end, a slight plastic deformation in the exposed core of the shunt cable, the cable connector and the coil connector, combine to positively secure all components, in a manner which withstands tension applied along the electrode, without elongation of the conductors or degradation of the electrical connection. At both ends, the electrical connection of the shunt cable core and the primary conductor coil is completed through the head of the cable connector. By contrast, along each shank and the remainder of the electrode length, dielectric sheath 200 electrically isolates shunt cable 194 from primary coil conductor 192. This is best seen in FIG. 9, illustrating the completely assembled electrode.

Sheath 200 is fluid impermeable, and is joined at its ends to the shunt connector shanks by fluid tight seals. Accordingly, the sheath and shunt connectors cooperate to. completely envelop cable 194, isolating it from any contact with body tissue or body fluids. Accordingly, while core 198 of the shunt cable preferably is formed of a body compatible material that is resistant to corrosion or other damage from contact with body fluids, such need not be the case. Other materials, perhaps not as body compatible but more highly conductive, can be considered for use as the shunt cable core. In either event, sheath 200 and the shunt connectors cooperate to protect the shunt cable against exposure to body fluids.

It is to be understood that end cap 180 and proximal coil connector 204 must be plastically deformable to enable crimping. It is preferred to provide an electrically conductive enlargement feature at the distal end of electrode 36, to counteract high current densities due to edge effects, and thus provide for a more uniform current distribution along the electrode. An electrically conductive end cap effectively suits this purpose.

Another factor in promoting uniform current distribution is the high conductivity of the electrode. Shunt cable 194 and primary coil 192 cooperate to provide two parallel conductive paths. This results in high conductivity, despite the relatively small diameter of electrode 36. The low impedance insures against any substantial voltage gradient across the electrode, even for electrodes in the range of 20–30 centimeters in length.

It is to be understood that electrodes 38 and 40 are assembled in substantially the same manner. The electrode structure provides a high degree of redundancy, particularly when the primary conductor coil is formed of several intermingled coils. In this event, one of the coils can break or otherwise fail without any noticeable degradation in electrode performance. Even in the event of a complete break in the primary coil, tissue stimulating pulses can be transferred to the coil via the shunt cable distal end. On a larger scale, the electrode array remains operable even in the event of a complete failure of one of the electrodes, with the remaining two electrodes cooperating to provide a desired effective electrode area for transferring signals through body tissue.

The junction body and electrode connectors provide for quick and convenient assembly of all components with reliable electrical and mechanical connections. The distal end caps of the electrodes perform the additional function of countering edge effects, for a more uniform current distribution over the length of each electrode. Thus, in accordance with the present invention there is provided an improved electrode array, particularly well suited for subcutaneous placement.

What is claimed is:

1. A body implantable tissue stimulating device, including:
   an elongate, flexible electrically conductive lead; and
   a tissue stimulating electrode array including at least two electrically common electrodes, each electrode including a body compatible primary conductor providing a convoluted electrically conductive path from a first end region of the electrode to a second and opposite end region of the electrode, a shunt conductor adjacent the primary conductor providing a substantially linear electrically conductive shunt path between said first and second end regions, said primary conductor and shunt conductor being electrically coupled at the first and second end regions and electrically isolated from one another between the first and second end regions;
   wherein the first end region of each electrode is coupled with respect to a distal end region of the lead, to enable the electrode to receive tissue stimulating electrical pulses from a pulse generating means at a proximal end of the lead.

2. The device of claim 1 wherein:
   said tissue stimulating electrode array includes three of said electrodes.

3. The device of claim 2 further including:
   means near the first end region and second end region of each electrode, for facilitating the attachment of each electrode to body tissue.

4. The device of claim 1 wherein:
   the primary conductor comprises a helically wound coil.

5. The device of claim 4 wherein:
the shunt conductor comprises a conductive cable, and the helically wound coil surrounds the cable.

6. The device of claim 5 further including:
a flexible, dielectric sheath surrounding the shunt conductor and surrounded by the helically wound coil.

7. The device of claim 6 further including:
a dielectric coating applied to the exterior surface of the cable between the first and second end regions.

8. The device of claim 6 further including:
first and second connecting means for electrically and mechanically coupling the cable and the coil at the first and second end regions, respectively.

9. The device of claim 8 wherein:
each of the first and second connecting means comprises an electrically conductive shunt connector mounted to the cable and surrounded by the helical coil along at least a portion of its length, and a coil connector surrounding the helical coil and the shunt connector for maintaining the coil against the shunt connector.

10. The device of claim 9 wherein:
the shunt connectors and coil connectors are tubular and plastically deformable.

11. The device of claim 10 wherein:
the coil connector is electrically conductive.

12. The device of claim 9 wherein:
the shunt connector surrounds the conductive cable, and the flexible and dielectric sheath surrounds and is attached to a portion of the shunt connector to form a fluid tight seal.

13. The device of claim 1 further including:
a means for providing a substantially fluid tight enclosure around the shunt conductor.

14. A body implantable tissue stimulation system, including:
a stimulation pulse generator;
a compliant, elongate tissue stimulating electrode array adapted to be implanted at least proximate the thoracic region, said electrode array including at least two electrically common electrodes, each electrode including a primary conductor providing a convoluted electrically conductive path from a first end portion of the electrode to a second and opposite end portion of the electrode, and a shunt conductor providing a substantially linear shunt path between said first end portion and said second end portion, said primary conductor and shunt conductor being electrically coupled at the first end portion and at the second end portion, said primary conductor being constructed of a biocompatible material and adapted to contact body tissue when said electrode is so implanted;
a first coupling means electrically coupling the tissue stimulating electrode array and the stimulation pulse generator;
a tissue stimulating electrode configuration including at least one electrode adapted to be implanted at least proximate the thoracic region and spaced apart from the first tissue stimulating electrode; and
a second coupling means, electrically isolated from the first coupling means, for coupling the stimulation pulse generator and the tissue stimulating electrode configuration.

15. The system of claim 14 wherein:
the tissue stimulating electrode array includes three electrically common electrodes substantially identical to one another, adapted to be implanted at least proximate the thoracic region in spaced apart relation to one another and electrically coupled to the stimulation pulse generator by the first coupling means.

16. The system of claim 15 wherein:
the first coupling means includes an electrically conductive lead having a proximal end coupled to the pulse generator, and a junction body connected to a distal end of the lead and to the three electrically common electrodes.

17. The system of claim 16 wherein:
said junction body includes an electrically conductive core and a biocompatible, dielectric casing surrounding the conductive core.

18. The system of claim 17 wherein:
the first coupling means further includes three electrically conductive lead extensions, each one of the extensions being coupled between the junction body and a corresponding different one of the three electrically common electrodes.

19. The system of claim 14 wherein:
the primary conductor comprises a helically wound coil, and the shunt conductor comprises a conductive cable surrounded by the coil.

20. The system of claim 19 further including:
a flexible, dielectrical and fluid tight sheath surrounding the conductive cable and surrounded by the coil.

21. The system of claim 20 further including:
first and second connecting means for mechanically and electrically coupling the conductive cable and the coil at the first and second end regions, respectively.

22. A body implantable tissue stimulating device, including:
an elongate, flexible electrically conductive lead; and
a tissue stimulating electrode array including at least two electrically common electrodes, each electrode including a body compatible primary conductor providing an electrically conductive path from a first end region of the electrode to a second and opposite end region of the electrode, the primary conductor having an exposed surface over the majority of its length for contact with body tissue;
a shunt conductor adjacent the primary conductor and providing a substantially linear electrically conductive shunt path between said first and second end regions;
a substantially fluid tight means surrounding the shunt conductor to isolate the shunt conductor from contact with body tissue or body fluids;
means electrically coupling the primary conductor and the shunt conductor at the first end region and at the second end region; and
wherein the first end region of each electrode is coupled with respect to a distal end region of the lead, to enable the electrode to receive tissue stimulating electrical pulses from a pulse generating means at a proximal end of the lead.

23. The device of claim 22 wherein:
said substantially fluid tight means surrounding the shunt conductor comprises a flexible and dielectric sheath surrounding the shunt conductor.

24. The device of claim 22 wherein:
the means for electrically coupling the primary conductor and shunt conductor include, at each of said and first and second end regions, an electrically conductive cable connector mounted to an end of the shunt conductor, and surrounded by and in contact with an end portion of the primary conductor.

25. The device of claim 22 further including:
means near the first end region and second end region of each electrode, for facilitating attachment of each electrode to body tissue.

26. The device of claim 25 wherein:
said means for facilitating attachment of each electrode comprise a distal cap at the distal end of each electrode and a strain relief sleeve at the proximal end region of each electrode;
each of the end caps including a suture opening, and each of the strain relief sleeves incorporating an annular suture groove.

* * * * *